US006297396B1

(12) United States Patent
Sas et al.

(10) Patent No.: US 6,297,396 B1
(45) Date of Patent: Oct. 2, 2001

(54) METHOD OF CRYSTALLIZING AND PURIFYING ALKYL GALLATES

(76) Inventors: Benedikt Sas, Steenweg op Ravels 209, 2360 Oud-Turnhout; Bruno Coppens, L. Carréstraat 73, 2220 Heist-op-den-Berg; Johan Van hemel, St. Theresiastraat 44, 2600 Antwerpen, all of (BE)

( * ) Notice: Subject to any disclaimer, the term of this patent is extended or adjusted under 35 U.S.C. 154(b) by 0 days.

(21) Appl. No.: 09/476,152

(22) Filed: Dec. 30, 1999

(51) Int. Cl.[7] ................................................. C07C 69/66
(52) U.S. Cl. ................................................................ 560/186
(58) Field of Search ............................................... 560/186

(56) References Cited

PUBLICATIONS

Theodore White, "Tannins–Their Occurrence and Significance", Read at the Agricultural Group Symposium on Polyphenols in Soils and Plants, Oct. 9, 1956, J. Sci. Food Agric., Jul. 8, 1957, 9 pages.

Y.J. Ahn, C.O. Lee, J.H. Kweon, J.W. Ahn, J.H. Park, "Growth–inhibitory Effects of Galla Rhois–derived Tannins on Intestinal Bacteria", 1998 The Society for Applied Microbiology, Journal of Applied Microbiology 84, 439–443.

Guojing Zhao, King–Thom Chung, Kimberly Milow, Wenxian Wang, S. Edward Stevens, Jr., "Antibacterial Properties of Tannic Acid and Related Compounds Against the Fish Pathogen Cytophaga Columnaris", Journal of Aquatic Animal Health 9:309–313, 1997.

*Primary Examiner*—Paul J. Killos
(74) *Attorney, Agent, or Firm*—Kent A. Herink; Daniel A. Rosenberg; Timothy G. Hofmeyer

(57) ABSTRACT

A method for synthesizing alkyl gallates. Gallic acid and an alkyl alcohol of the order of the desired gallate are heated in a reaction vessel in the presence of a catalyst such as sulfuric acid or para-toluene sulfonic acid. Water is generated, forming an azeotrope with the alkyl alcohol. Distillation or Soxhlet extraction using a drying agent removes the formed water. Upon completion of the reaction, the reaction mixture is added while stirring to an alkane solvent and cooled to produce crystals of the desired alkyl gallate. The crystals may be further recrystallized and washed to improve their purity.

13 Claims, 12 Drawing Sheets

METHOD OF CRYSTALLIZING AND PURIFYING ALKYL GALLATES

BACKGROUND OF THE INVENTION

1. Field of the Invention

The invention relates generally to a method of crystallizing and purifying alkyl gallates and, more specifically, to a method of crystallizing and purifying esters of gallic acid or 3,4,5-trihydroxybenzoic acid.

2. Background of the Prior Art

Gallic acid, or 3,4,5-trihydroxybenzoic acid, is often obtained by acid or alkaline hydrolysis of tannins, which are natural substances, widespread and readily available in the environment. White, T. *Of the Science of Food and Agriculture*, 1957, 8, 377. Gallic acid can also be obtained via hydrolysis of spent broths from *Aspergillus niger* or *Penicillium glaucum*. This trihydroxybenzoic acid can be transferred by esterification with alcohol into the methyl, propyl, or lauryl ester, which are all widely used food and feed antioxidant additives.

Some of these esters can also be found as such in nature. Methyl gallate is one of the biologically active components of Galla Rhois. Ahn, Y.-S.; Kmeon, J.-H. *J. of Applied Microbiology*, 1998, 84, 439. In addition to their strong antioxidant effects, gallates also exhibit quite powerful antimicrobial activities. Ahn, Y.-S.; Kmeon, J.-H. *J. of Applied Microbiology*, 1998, 84, 439; Stevens, S. E. *J. of Aquatic Animal Health*, 1997, 9, 309.

This wide range of biological activities of gallates has generated interest in them for commercial application. Unfortunately, the prior art method of synthesis by esterification of gallic acid, including the steps of purification and crystallization, is rather complex and difficult, with the result that the gallates are expensive to produce and to use.

Although several production methods of relatively pure crystals of alkyl gallates are described in the prior art, all methods for the synthesis of higher alkyl gallates (n>5) are rather impractical for large production purposes, result in a product that is difficult to purify, and/or require toxic and expensive solvents to remove the formed water azeotropically. There is, accordingly, a need for a simple and cost effective general synthesis method for the production of a variety of gallates, particularly higher order gallates, with high purity.

SUMMARY OF THE INVENTION

Alkyl gallates are synthesized by reacting gallic acid with an alkyl alcohol in the presence of a catalyst such as hydrochloric acid, sulfuric acid or, preferably, p-toluenesulfonic acid. The reaction is carried out at a temperature of between about 100° C. and 180° C. under atmospheric or reduced pressure to remove the formed water and drive the reaction toward formation of the gallate. The reaction is allowed to proceed to satisfactory completion, whereupon the temperature of the reaction mixture is reduced to an intermediate temperature while stirring and then added to a solvent that is at the approximately the same intermediate temperature. The temperature of the mixture is reduced to ambient. Gallate crystals form in the solvent and are filtered out. The gallate crystals can be washed and recrystallized to remove impurities.

In the preparation of octyl gallate, octyl alcohol is heated in a reactor to 60° C. and gallic acid is added in a molar ratio of 1:3. A small amount of p-toluenesulfonic acid is added as a catalyst. The mixture is submitted to reaction in a Rotavapor at a temperature of 160° C. and a vacuum of −0.4 bar. The azeotrope water/octyl alcohol is distilled for approximately 5 to 6 hours. The remaining reaction mixture is cooled to approximately 55° C. while stirring. In another reactor, petroleum ether (boiling point 40–60° C.) is heated to approximately 55° C. When both the petroleum ether and the reaction mixture have reached the same temperature, the reaction mixture is added to the petroleum ether while stirring. The mixture is allowed to cool to room temperature over a period of approximately 5 hours. The octyl gallate crystallizes and the impure octyl gallate crystals are recovered by filtration. The crystals are washed with room temperature petroleum ether. Drying of the washed octyl gallate crystals for 24 hours at approximately 60° C. under vacuum results in octyl gallate of approximately 95% purity at a yield of approximately 75%.

Purity of the gallate crystals can be improved by washing the crystals with water following the initial washing with petroleum ether, and then washing the crystals with petroleum ether again.

In an alternative embodiment, after the reaction has proceeded to the point where the gallic acid content is less than a desired amount, preferably 1%, the mixture is neutralized by the addition of an aqueous alkaline solution. The neutralized reaction mixture is cooled to approximately 70° C., and then washed with water or, preferably, a solution of water and NaCl. The washed reaction mixture is cooled to approximately 55° C. Petroleum ether in a volume of approximately twice the volume of the reaction mixture heated to 55° C. is added to the reaction mixture. The mixture is then cooled while stirring to crystallize the octyl gallate. The mixture is filtered and the crystals are washed once with water and once with petroleum ether. After filtration, the crystals are dried in vacuo.

The distilled azeotrope water/alkyl alcohol mixture can be separated and the alcohol reused. Also, the petroleum ether can be recovered by vacuum distillation and reused in succeeding syntheses.

It is an object of the invention to provide a simple and economical method for synthesizing alkyl gallates having a high purity.

DETAILED DESCRIPTION OF PREFERRED EMBODIMENTS

Figure 1:
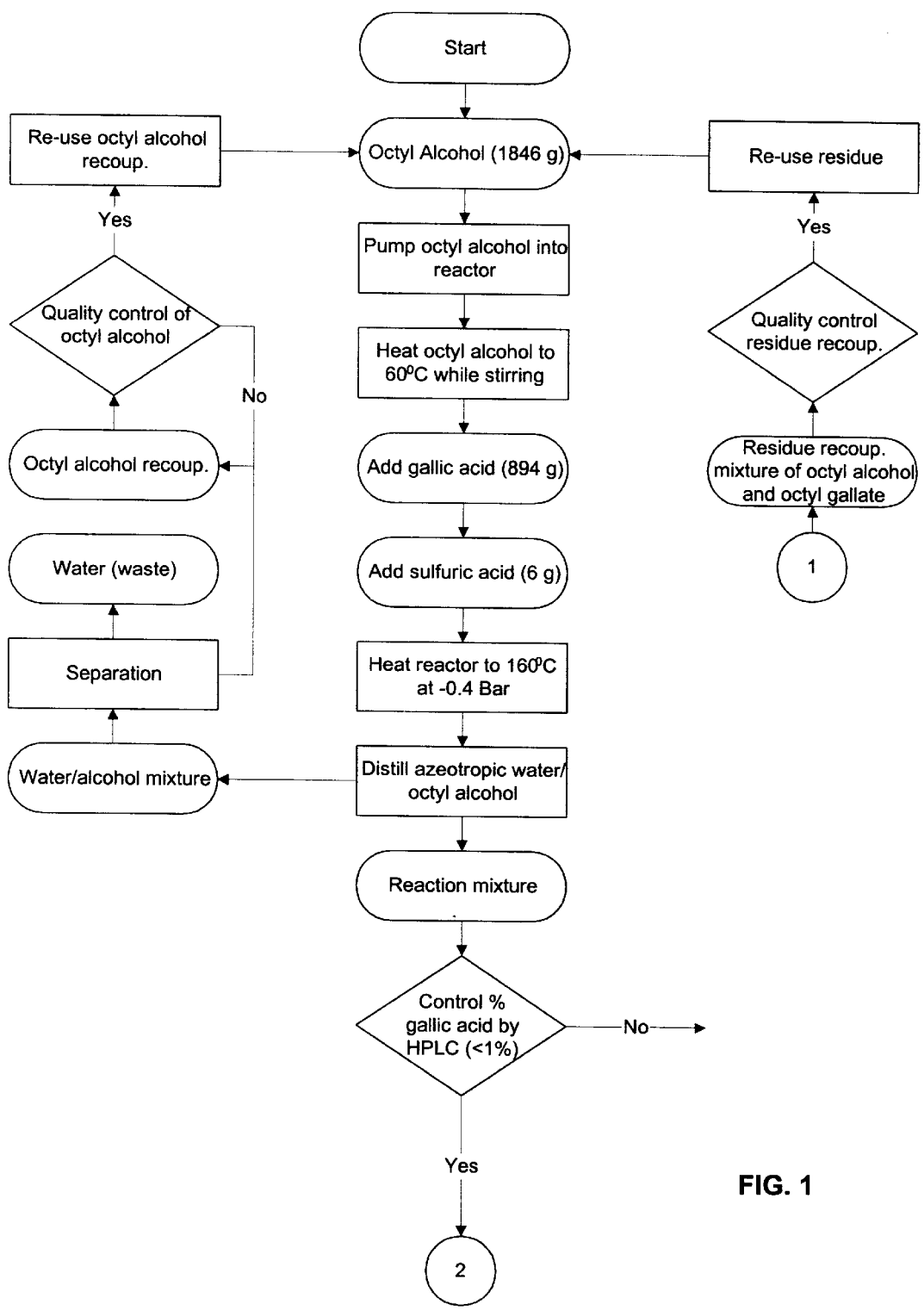
FIGS. 1 and 2 comprise a flowchart of a reaction process of the present invention.

This invention relates to a method for synthesizing relatively pure crystals of alkyl gallates from gallic acid, 3,4,5-trihydroxybenzoic acid. This method, more specifically, relates to a method of reacting gallic acid and an alkyl alcohol in the presence of a catalyst to form the corresponding alkyl gallate in a relatively pure form at high yields.

Essentially pure gallic acid is available from a number of sources. It is produced by the action of mold on tannins or by boiling of tannins with a strong acid or caustic soda. Esterification of gallic acid with an alkyl alcohol using the present method results in the production of the corresponding alkyl gallate. Existing economical methods exist for the production of short chain (n<5) gallates, however, so that the preferred products of the present synthesis method are higher order gallates.

The esterification of gallic acid and octyl alcohol is represented below

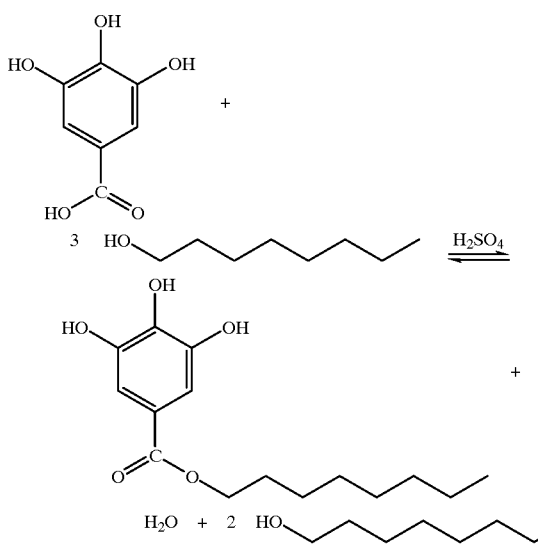

The sulfuric acid is a catalyst and need be present only in small (<1%) amounts.

As used in this application, petroleum ether means refined, partly refined, or unrefined petroleum products and liquid products of natural gas, not less than 10% of which distill below 175° C. and not less than 95% of which distill below 240° C. when subjected to distillation in accordance with ASTM D86 and having a boiling point between about 40° C. and about 60° C.

The steps of the present method include placing an alkyl alcohol in a reactor and heating it to approximately 60° C. To assist in driving the reaction toward the formation of the gallate, an excess molar ratio of alkyl alcohol is used. While the ratio of alkyl alcohol to gallic acid can be varied through a broad range, it has been found that a ratio of about three moles of alkyl alcohol to one mole of gallic acid is preferred. The gallic acid is added to the alkyl alcohol together with a small amount (<1%) of a catalyst, such as sulfuric acid or p-toluene sulfonic acid. The mixture is submitted to reaction in a Rotavapor at a temperature of 160° C. and a vacuum of −0.4 bar. The azeotrope water/alkyl alcohol is distilled and the quantity of water formed and collected can be measured to monitor the progress of the reaction. Alternatively, the remaining unreacted gallic acid can be measured by high performance liquid chromatography (HPLC). As the reaction moves to completion and the amount of gallic acid remaining gets small, the reaction tends to form dioctyl ether so the reaction is stopped when the economics of having unreacted gallic acid are balanced with the increasing production of the dioctyl ether byproduct, somewhere around 1% remaining gallic acid.

After the reaction has proceeded to satisfactory completion, the remaining reaction mixture is cooled to approximately 55° C. while stirring. In another reactor, petroleum ether (boiling point 40–60° C.) is heated to approximately 55° C. When both the petroleum ether and the reaction mixture have reached the same temperature, the reaction mixture is added to the petroleum ether while stirring. The mixture is allowed to cool slowly to room temperature. The alkyl gallate crystallizes and the alkyl gallate crystals are recovered by filtration. The crystals are washed with room temperature petroleum ether. Drying of the washed alkyl gallate crystals under vacuum results in alkyl gallate of high purity at a high yield.

EXPERIMENT 1

Method for the Synthesis of Octyl Gallate

One-thousand, eight hundred, forty-six grams (1846 g) of technical octyl alcohol (14.2 mole) was heated in a reactor of 2 L to a temperature of 60° C. Eight hundred, ninety four grams (894 g) of gallic acid was added (10% moisture) (4.73 mole) and approximately 6 g of sulfuric acid (96%) was added as a catalyst. The mixture was submitted to reaction in a Rotavapor (Heidolph) at a temperature of 160° C. and a vacuum of −0.4 bar. While reacting, the azeotrope water/octyl alcohol [(water Bp. 100° C. (90%)/octyl alcohol Bp. 195.15° C. (10%)) azeotrope Bp. 99.4° C.] is distilled off and contains at least 174.5 g of water. Five to 6 hours were needed for completion. The percentage of remaining gallic acid can be controlled by high-performance liquid chromatography (HPLC). When the remaining gallic acid is less than 1% the process can be taken to the next step.

The distilled azeotropic water/octyl alcohol mixture is separated by means of a separation funnel and the octyl alcohol is re-used after quality control by gas chromatography (GC). The remaining reaction mixture is cooled down to approximately 55° C., while stirring. In another reactor of 6 L with reflux condenser and stirrer, 5500 ml of petroleum ether (Bp. 40–60° C.) is heated to approximately 55° C. When both the petroleum ether and the reaction mixture have the same temperature (approximately 55° C.), the reaction mixture is slowly added to the petroleum ether while stirring. The mixture of the reactants and the petroleum ether is cooled down to room temperature over a period of approximately 5 hours, (hour 0, temp. 55° C.; h. 0.5, temp. 60° C.; h. 1, temp. 55° C.; h.2, temp. 45° C.; h3, temp. 35° C.; h. 4, temp. 25° C.; h. 5, temp. 25° C.). The octyl gallate will crystallize and can be filtered off via a vacuum sucked glass filter. Solid impure octyl gallate and filtrate A (octyl gallate, octyl alcohol and petroleum ether) are obtained. The solid impure octyl gallate is mixed again with 2750 ml of petroleum ether (Bp. 40–60° C.), but this time at room temperature. Again a vacuum sucked glass filter filters off this mixture. Pure octyl gallate and filtrate B (octyl gallate, octyl alcohol and petroleum ether) are obtained.

Figure 2:
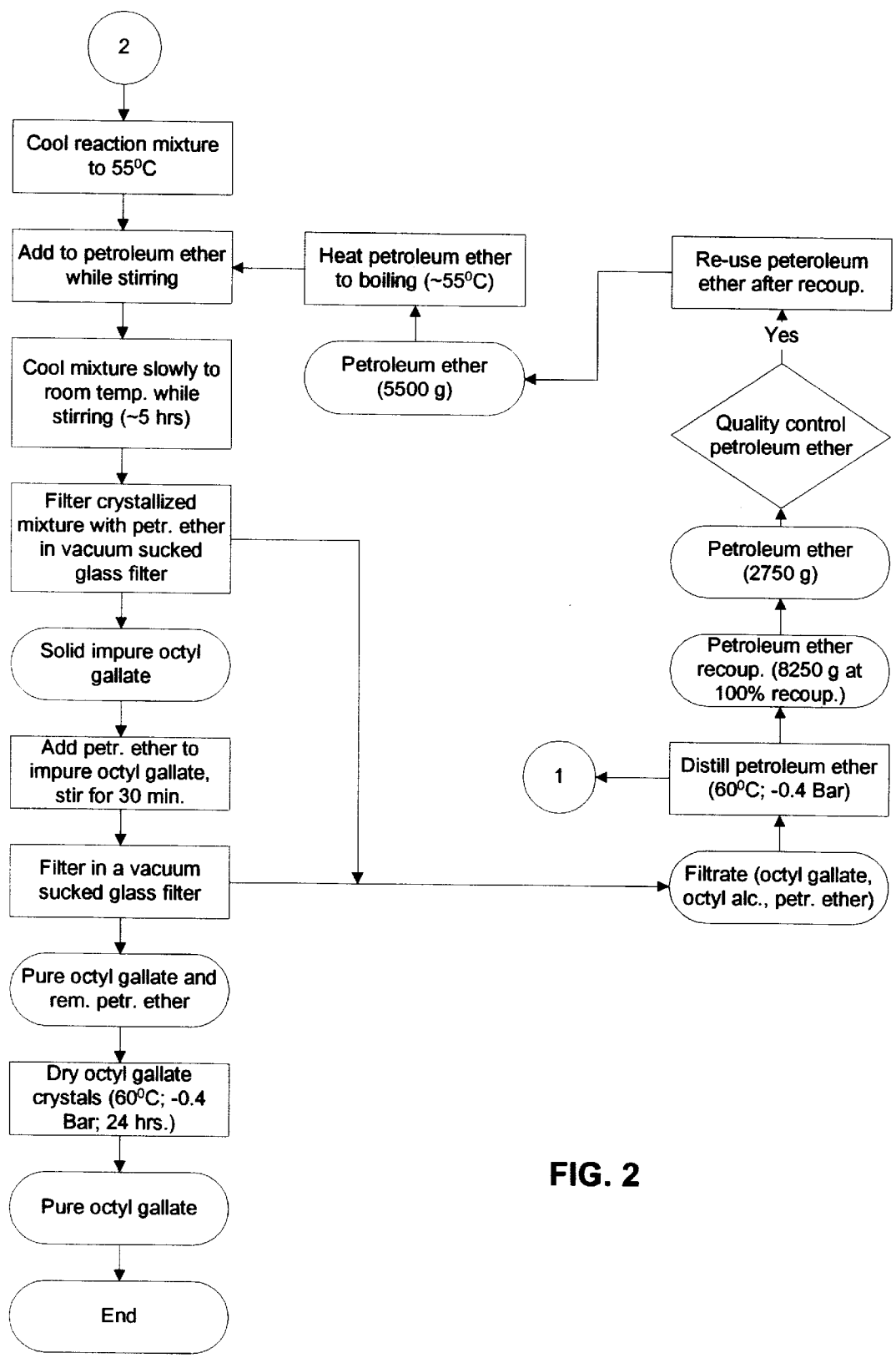
Figure 3:
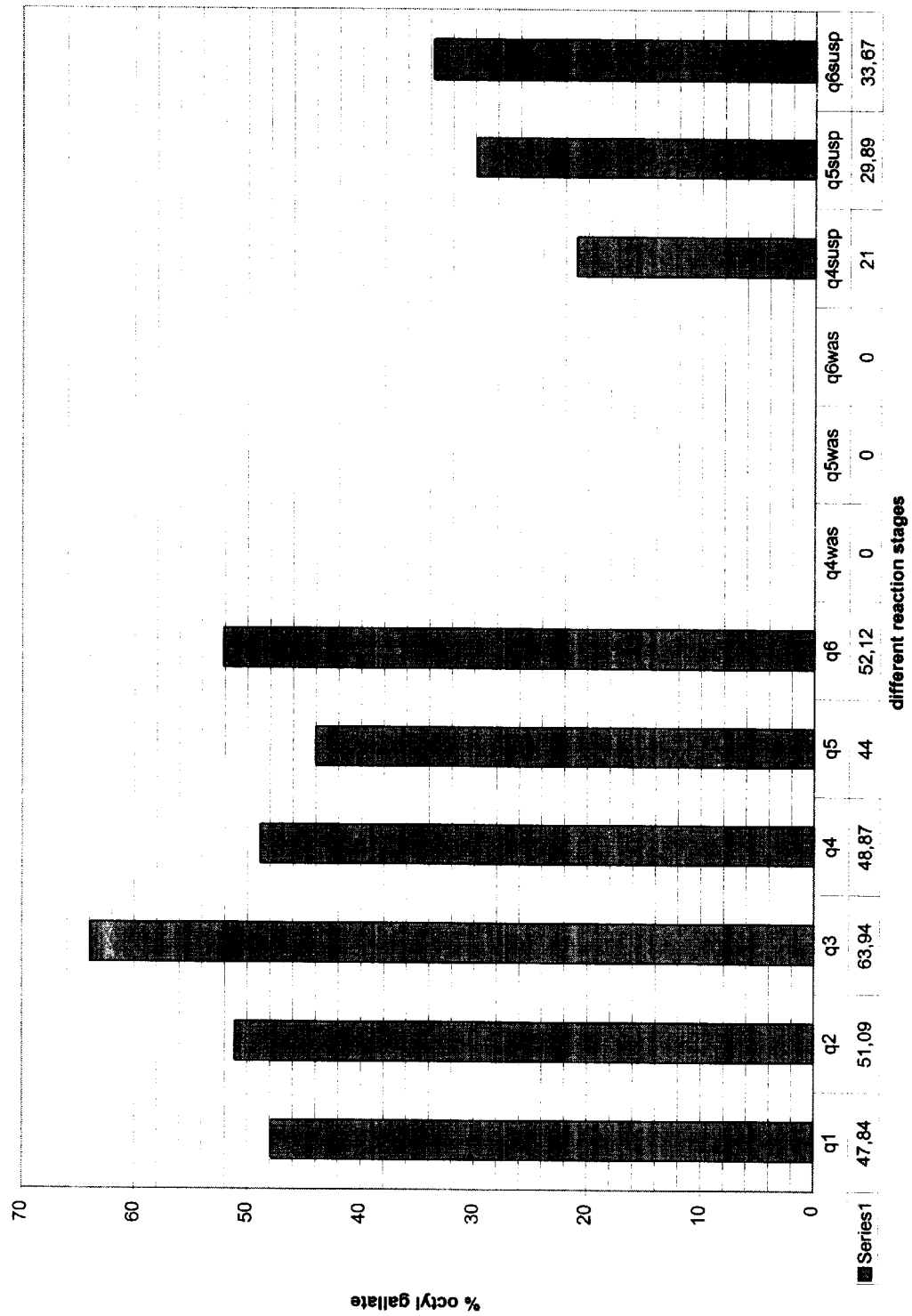
FIG. 3 is a graphical representation of the percentage of octyl gallate present at various stages of a reaction.
Figure 4:
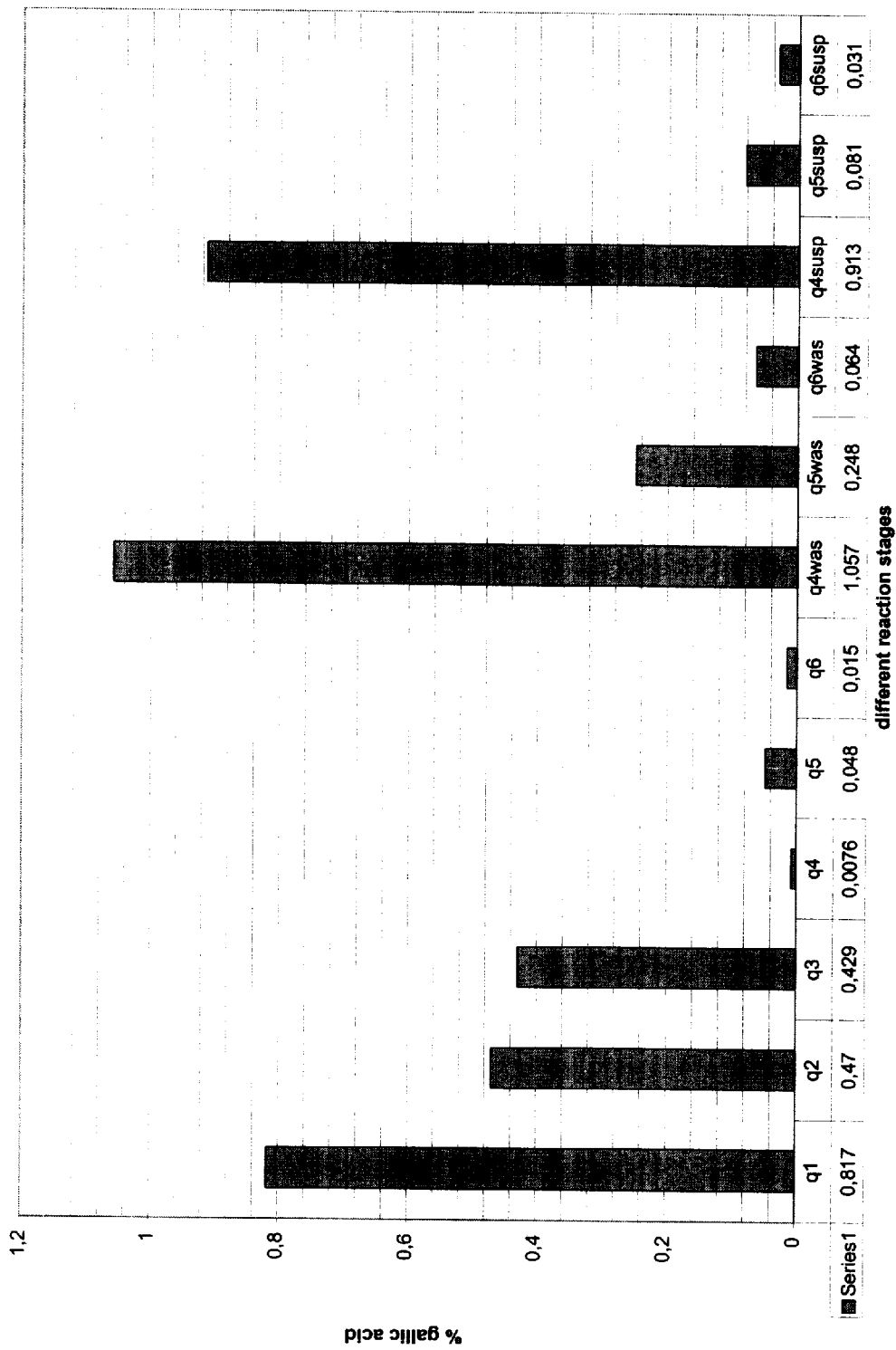
FIG. 4 is a graphical representation of the percentage of gallic acid present at various stages of the reaction of FIG. 3.
Figure 5:
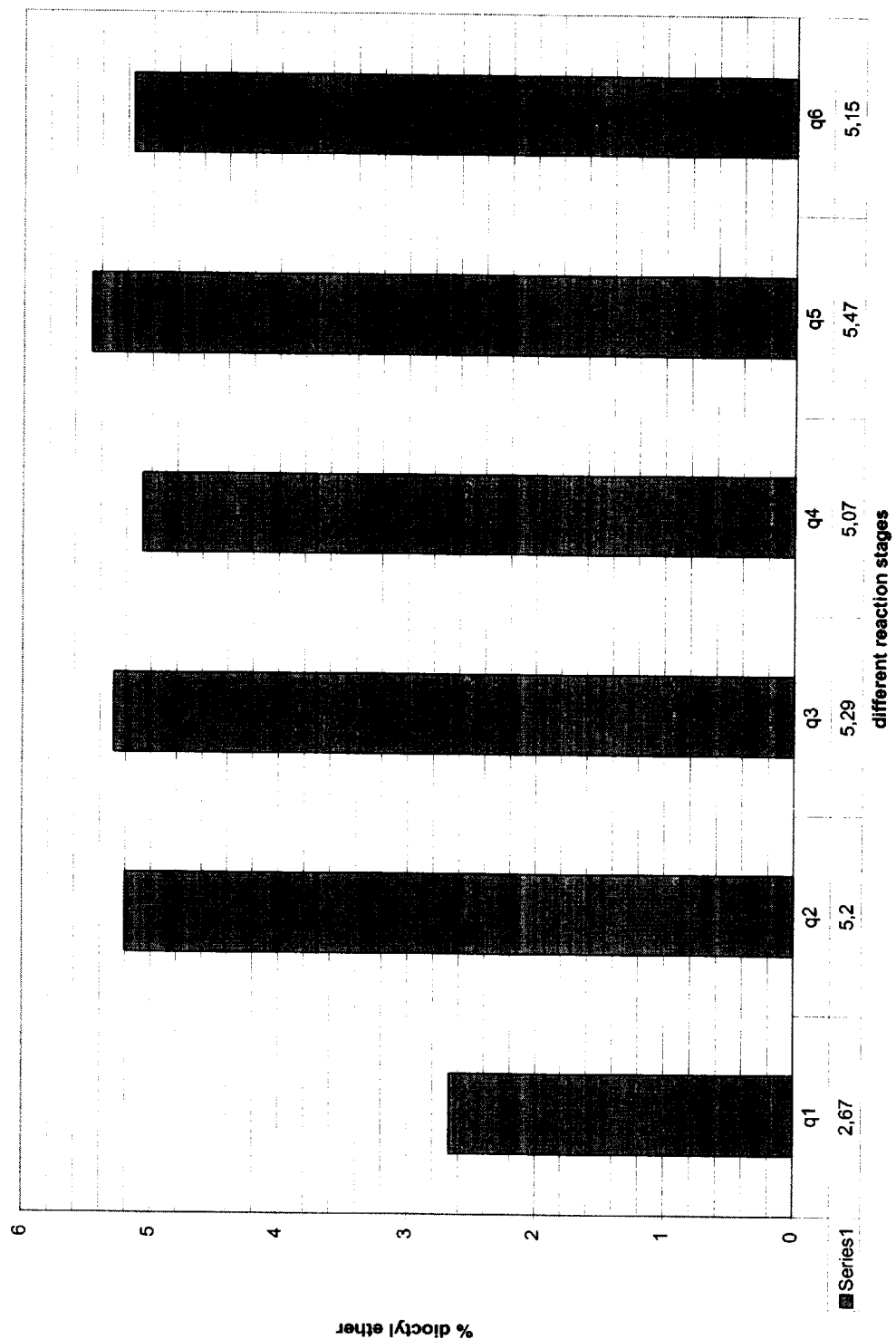
FIG. 5 is a graphical representation of the percentage of dioctyl ether present at various stages of the reaction of FIG. 3.
Figure 6:
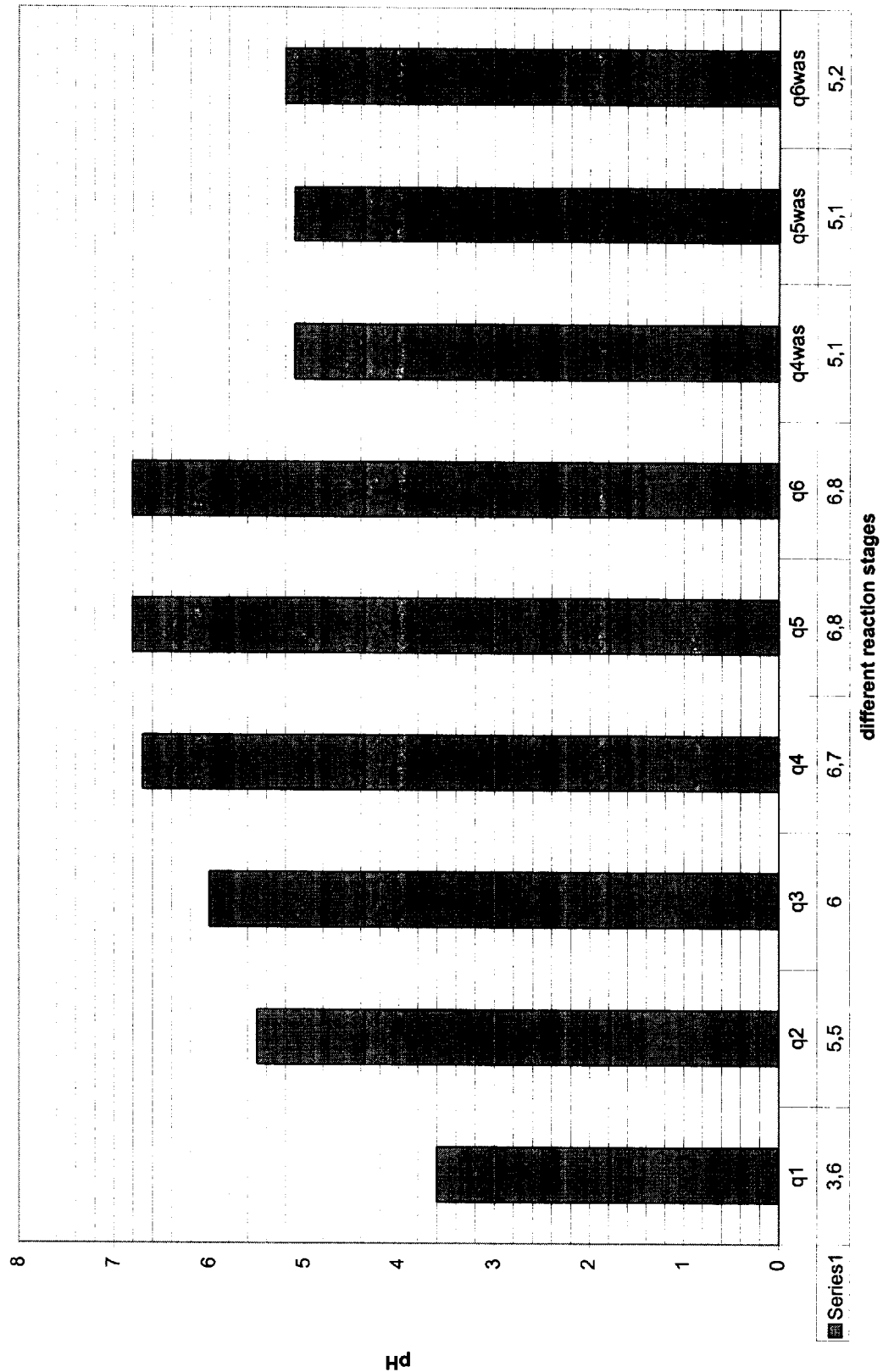
FIG. 6 is a graphical representation of the pH at various stages of the reaction of FIG. 3.

Filtrate A and B are combined and the petroleum ether is recovered via vacuum distillation with a Rotavapor (temp. 60° C., vacuum −0.4 Bar). After quality control for impurities, the petroleum ether can be re-used; experience with the present method is that there is only a very low level of impurities in the recovered petroleum ether so that it can be reused many times. HPLC and GC also control the residue for the percentage of octyl gallate and octyl alcohol, and it is re-used at the start of the reaction. Drying of the pure octyl gallate for 24 hours at approximately 60° C. and at a vacuum of −0.4 Bar in a vacuum oven, yielded 1000g octyl gallate of approximately 95% purity (yield: 75%) as determined by HPLC. The product is light white to gray colored very fine needles that are slightly electrostatic. A flow diagram of the process described in this Experiment 1 is set out in FIGS. 1 and 2.

It was found that cooling to 0° C. during crystallization increases the yield (from 75% to 81%) but decreases the purity (from 95% to 86%).

To obtain a pure product, it is important that the reaction mixture is first dissolved totally in the petroleum ether before it is crystallized. This is achieved by having the reaction mixture and the petroleum ether heated to 60° C. before letting the blend cool down to room temperature. Also, the petroleum ether and the reaction mixture should have substantially the same temperature when being blended.

The quality of the end product was evaluated by comparing it against the product Progallin O® of Nipa Laboratories Ltd. The water content (Karel Fischer method), total % moisture, the % gallic acid and octyl gallate remaining (by HPLC), pH (1 g of product dissolved in 100 ml water), melting point (Buchi 510), UV and IR spectra, and pack density were all measured. The results are set out in Table 1 below.

While hexane produced crystals of a high purity, it is more expensive and more toxic than petroleum ether. While petroleum ether is the preferred solvent, all types of alkane solvents can be used, even benzene or toluene.

Tests were also conducted in which the ratio of reaction mixture to petroleum ether was varied, specifically the ratios 1:1, 1:2, and 1:3 (volume:volume). The purity of the octyl gallate did not increase significantly with large ratios of petroleum ether, but it was discovered that a ratio in the range of approximately 1:2 is needed in order to dissolve everything.

Above 60° C., i.e., above the boiling point of the petroleum ether, the crystallization stage can be hazardous. The reaction mixture becomes solid below about 40° C. In the preferred embodiment, a starting temperature of about 55° C., i.e., the boiling point of the petroleum ether, is used.

When adding the petroleum ether to the cooled reaction mixture to begin crystallization, if the petroleum ether is at room temperature, the reaction mixture does not dissolve very well in the petroleum ether and would risk the inclusion of substantial amounts of impurities in the final product. It is preferred to heat the petroleum ether to its boiling point (55° C.) so the reaction mixture will dissolve readily and result in a higher purity end product.

It was observed that a minimum of two hours is needed to complete crystallization. Further, vigorous stirring yields smaller crystals, which results in reduced inclusion of impurities in the crystal matrix.

To determine the effect of temperature on yield and purity, the following test was conducted. A reaction mixture of a 1:4 mole equivalent ratio reaction (conversion factor 100% and 44% octyl gallate) is crystallized in a 1:2 volume ratio with petroleum ether. In trial A, the temperature was reduced to room temperature (25° C.) and in trial B to 0° C.

TABLE 1

| Tests | Progallin O ® (Nipa) | Synthesized Octyl Gallate |
| --- | --- | --- |
| % water | 0.23% | 0.46% |
| % moisture | 0.18% | 0.89% |
| % gallic acid | 0.04% | 1.1% |
| % octyl gallate | 90.74% | 97.49% |
| pH (1 g/100 ml water) | 6 | 3.70 |
| Melting point | 101° C. | 91° C. |
| U.V. spectroscopy | 218,274 (λmax, nm) | 218,274 (λmax, nm) |
| I.R. spectroscopy | (KBr, pellets) 3450, 3340 2920, 2860, 1670, 1605, 1525, 1455, 1400, 1370, 1305, 1255, 1195, 1090, 1020, 985, 970, 935, 875, 860, 825, 770, 745, 735, 715, 635 (λmax, cm$^{-1}$) | (KBr, pellets) 3445, 3340 2920, 2860, 1670, 1610, 1530, 1460, 1400, 1375, 1305, 1260, 1200, 1090, 1050, 1020, 1000, 990, 970, 935, 875, 860, 825, 770, 745, 735, 715, 640 (λmax, cm$^{-1}$) |
| Pack density | 0.667 | 0.455 |

The octyl gallate synthesized under the present method is very similar to the Progallin O® product. The differences in melting point and pH can be explained by the 1.1% gallic acid remaining in the product and the larger moisture content. If the synthesized product is washed with water, followed by washing in petroleum ether, a product with a melting point of 95° C. and pH of 5.5 is obtained. The remaining amount of gallic acid was determined to be less than 0.5%.

Tests were done on the crystallization steps. Rather than petroleum ether, the crystallization was carried out with one of chloroform, methylene chloride and hexane. The use of chloroform or methylene chloride resulted in a loss of purity.

TABLE 2

|  | Trail A | Trail B |
| --- | --- | --- |
| Temp. of PE | 55° C. | 55° C. |
| Temp. of reaction mixture | 55° C. | 55° C. |
| Cooling to | 25° C. | 0° C. |
| Time of cool down | 3 h | 3 h |
| Yield | 63.6% | 81.8% |
| Purity | 108% | 88% |
| Octyl gallate remaining in liquid residue | 13% | 3.5% |

From Table 1 it can be seen that the lower the final temperature, the higher the yield, but the lower the purity.

The finished product of Experiment 1 above was washed with water, followed by washing with petroleum ether. The octyl gallate was obtained as a crystalline white powder with a purity of approximately 100%. It had a melting point of 95° C. and a 1% solution in water had a pH of 5.5. The remaining amount of gallic acid was less than 0.5%.

EXPERIMENTS 2–3
Formation and Purification of Lauryl Gallate

To examine the capabilities of the novel method of forming gallates, it was attempted to form gallates of order 2 through 6. The methods and conditions used and the results are discussed in detail in U.S. Pat. application Ser. No. 09/427,948 which is incorporated herein by this reference. Two methods of synthesizing lauryl gallate are described below.

EXPERIMENT 2
Synthesis of Lauryl Gallate

Lauryl alcohol in the amount of 294.4 g was heated in a flask of 1 L to a temperature of 60° C. One hundred grams (100 g) of gallic acid was added (purity 90%) together with 1 ml of sulfuric acid (96%) as a catalyst. The mixture was submitted to reaction in a Rotavapor at a temperature of approximately 160° C. and a vacuum of −0.4 bar. While reacting, the azeotropic water/lauryl alcohol was distilled off. Approximately 5 to 6 hours were needed for completion. The percent of remaining gallic acid was controlled by HPLC. When the remaining gallic acid was less than 1%, the process can be taken to the next step. The distilled azeotropic water/lauryl alcohol mixture was separated by means of a separation funnel and the lauryl alcohol can be re-used after quality control by GC. The remaining reaction mixture was cooled down to approximately 55° C., while stirring. In another flask of 2 L with reflux cooler and stirrer, 1 L of petroleum ether (Bp. 40–60° C.) was heated to approximately 55° C. When both the petroleum ether and the reaction mixture had the same temperature (approximately 55° C.), the reaction mixture was slowly added to the petroleum ether while stirring. The mixture of the reactants and the petroleum ether was cooled down over a period of approximately 5 hours to room temperature (hour 0, temp. 55° C.; h. 0.5, temp. 60° C.; h. 1, temp. 55° C.; h.2, temp. 45° C.; h3, temp. 35° C.; h. 4, temp. 25° C.; h. 5, temp. 25° C.). The lauryl gallate crystallized and was filtered via a vacuum sucked glass filter. Solid impure lauryl gallate and filtrate A (lauryl gallate, lauryl alcohol, petroleum ether) were obtained. The solid impure lauryl gallate was mixed again with 0.5 L of petroleum ether (Bp. 40–60° C.), but this time at room temperature. Again, this mixture was filtered by a vacuum sucked glass filter. This time pure lauryl gallate and filtrate B (lauryl gallate, lauryl alcohol, petroleum ether) were obtained. Filtrate A and B were combined and the petroleum ether was recovered via vacuum distillation with a Rotavapor (temp. 60° C., −0.4 Bar). After quality control, the petroleum ether could be re-used. The residue was also checked for remaining lauryl gallate and lauryl alcohol by HPLC and GC, it can be re-used at the start of a next batch. Drying of the pure lauryl gallate for 24 hours at approximately 60° C. and at a vacuum of −0.4 Bar in a vacuum oven, yields crystalline lauryl gallate. Lauryl gallate was obtained as a crystalline silver white powder with a purity of 81.35%. The conversion rate was rather good as only 0.2% of gallic acid was found remaining in the reaction mixture.

EXPERIMENT 3
Synthesis of Lauryl Gallate (alternative method)

The method of Experiment 2 was optimized. In this method, the finished product of Experiment 2 was washed with water followed by washing with petroleum ether (55° C.) and filtering immediately while hot. Lauryl gallate was obtained as a crystalline white powder with a purity of approximately 100% and a melting point of 97° C.

The results of Experiments 2 and 3 are summarized in Table 3 from which, together with the data on the formation of gallates of lower order in the above-incorporated patent application, it can be seen that the present method provides a new synthesis method for the formation of a wide range of gallates.

TABLE 3

| Product Synthesized | Purity % | Yield % | Gallic acid remaining after 8 h in reaction mixture % | Conversion % | Mp ° C. | Retention time GCMS Min |
|---|---|---|---|---|---|---|
| Octyl gallate | 95 | 75 | <1 | 99 | 91 | ND |
| Lauryl gallate | 81.35 | ND | 0.2 | ND | ND | ND |
| Lauryl gallate | 100 | ND | 0.2 | ND | 97 | ND |

ND: not determined

EXPERIMENTS 4a–c
Influence of Washing Water Temperature on Reaction Kinetics.

The reaction mixture of Experiment 1 was initially washed with an equal volume of 55° C. water. The reaction mixture was then washed a second time with an equal volume of 55° C. water. The pH of the initial washing water was 1.8, and the pH of the second washing water was 2,4. The melting point of the end product was less than 97° C., and the pH of a 1% solution of the end product in 100 ml water was 4.5.

The reaction mixture of Experiment 1 was initially washed with an equal volume of a 0.23% NaOH aqueous solution at a temperature of 55° C. The reaction mixture was then washed a second time with an equal volume of 55° C. water. The pH of the initial washing solution was 4.5, and the pH of the second washing water was 4.5. The melting point of the end product was less than 97° C., and the pH of a 1% solution of the end product in 100 ml water was 6.6.

The reaction mixture of Experiment 1 was initially washed with an equal volume of a 0.5% NaHCO$_3$ aqueous solution at a temperature of 55° C. The reaction mixture was then washed a second time with an equal volume of 55° C. water. The pH of the initial washing solution was 4.4, and the pH of the second washing water was 4.3. The melting point of the end product was less than 97° C., and the pH of a 1% solution of the end product in 100 ml water was 6.7.

EXPERIMENTS 5a–b
Effect of Neutralizing Agent and Washing Solutions on Reaction Kinetics The reaction mixture of Experiment 5a was made by the method of Experiment 1, with the following parameters: 1 atm, 140° C., 4.0 kg gallic acid, 8.24 kg octyl alcohol, 0.124 kg PTSA. The octyl alcohol was preheated to 80° C. before adding the gallic acid.

In an attempt to minimize the amount of diocytl ether formed, the PTSA was added at 95° C. The reaction mixture was neutralized with a 50% NaOH aqueous solution at 140° C. The concentration was selected to limit the development of vapors upon the addition of the neutralizing agent to the reaction mixture and the temperature was selected in an attempt to neutralize the reaction mixture quickly and limit the formation of dioctyl ether. The amount of the neutralizing agent was selected to provide a 1.0 molar equivalent of NaOH to a 1.0 molar equivalent of all available acid (PTSA and gallic acid). The reaction mixture was then washed with an equal volume of water at 75° C. Before the washing step, the reaction mixture of Experiment 5a was tested and observed to be 51.85% octyl gallate, 0.075% gallic acid, 3.614% dioctyl ether, and had a pH of 8.1.

The reaction mixture of Experiment 5b was made by the method of Experiment 1, with the following parameters: 1 atm, 140° C., 4.0 kg gallic acid, 8.24 kg octyl alcohol, and 0.124 kg PTSA. The octyl alcohol was preheated to 80° C. before adding the gallic acid.

In an attempt to minimize the formation of dioctyl ether, the PTSA was added at 95° C. The reaction mixture was neutralized with a 50% NaOH aqueous solution at 140° C. The concentration was selected to limit the development of vapors upon the addition of the neutralizing agent to the reaction mixture and the temperature was selected in an attempt to neutralize the reaction mixture quickly and limit the formation of dioctyl ether. The amount of the neutralizing agent was selected to provide a 1.0 molar equivalent of NaOH to a 1.0 molar equivalent of PTSA. The reaction mixture was then washed first with 4 kg of water and then twice with 2 kg of water, each time at 75° C.

For the purposes of illustrating the results of Experiment 5b graphically in FIGS. 3–6, the different stages of the reaction are assigned the following designations: Q1=reaction mixture before washing; Q2=reaction mixture neutralized 1; Q3=reaction mixture neutralized 2; Q4=reaction mixture washed 1; Q5=reaction mixture washed 2; Q6=reaction mixture washed 3; Q4was=wash water 1; Q5was=wash water 2; Q6was=wash water 3; Q4susp=suspended wash layer 1; Q5susp=suspended wash layer 2; and Q6susp=suspended wash layer 3.

Washing of the reaction mixture is used to improve the purity of the octyl gallate. To avoid pushing the reaction in the reverse direction, the reaction mixture is neutralized to a pH of approximately 6 before the excess of water is added for washing. In the described example, one mole equivalent of NaOH to one mole equivalent of PTSA is used in the form of a 50% NaOH aqueous solution added to the 140° C. reaction mixture at the end of the reaction. The high temperature is used to attempt to end the reaction quickly and avoid the formation of dioctyl ether. After neutralization, the reaction mixture is cooled to approximately 70° C. and then washed three times with a 10% NaCl solution; once with 2 volumes of NaCl solution to 6 volumes of the reaction mixture and twice with one volume of NaCl solution to 6 volumes of the reaction mixture. Testing of the densities of different concentrations of brine solutions over the range of temperatures applicable to the present method of synthesis using standard laboratory techniques resulted in the selection of a 10% NaCl solution although the exact concentration is not critical. The washing is preferably carried out at 70° C. because at this temperature the reaction mixture is still liquid and at substantially lower temperatures, the reaction mixture would cool down to a temperature where the octyl gallate would not stay in solution. Further, the higher the temperature, the greater the difference in density between the brine solution and the reaction mixture, which improves separation. With a 10% brine solution, separation at 70° C. is improved over plain water and smaller suspension layers are formed. The concentration of the NaCl solution was determined by trying a variety of concentrations and temperatures to improve the separation of layers and to avoid the formation of intermediate or suspended layers.

EXPERIMENT 6
Influence of Different Cooling Temperatures on Purity and Yield.

Seven different tests were done. In every test one volume part of the reaction mixture was brought to a temperature of 55° C. while stirring. Concurrently, two volume parts of petroleum ether were heated until also 55° C. When both of these liquids were at 55° C., the reaction mixture was slowly added to the petroleum ether while stirring at 500 rev/min. This mixture was stirred at this rate for 30 min at 55° C.

Figure 7:
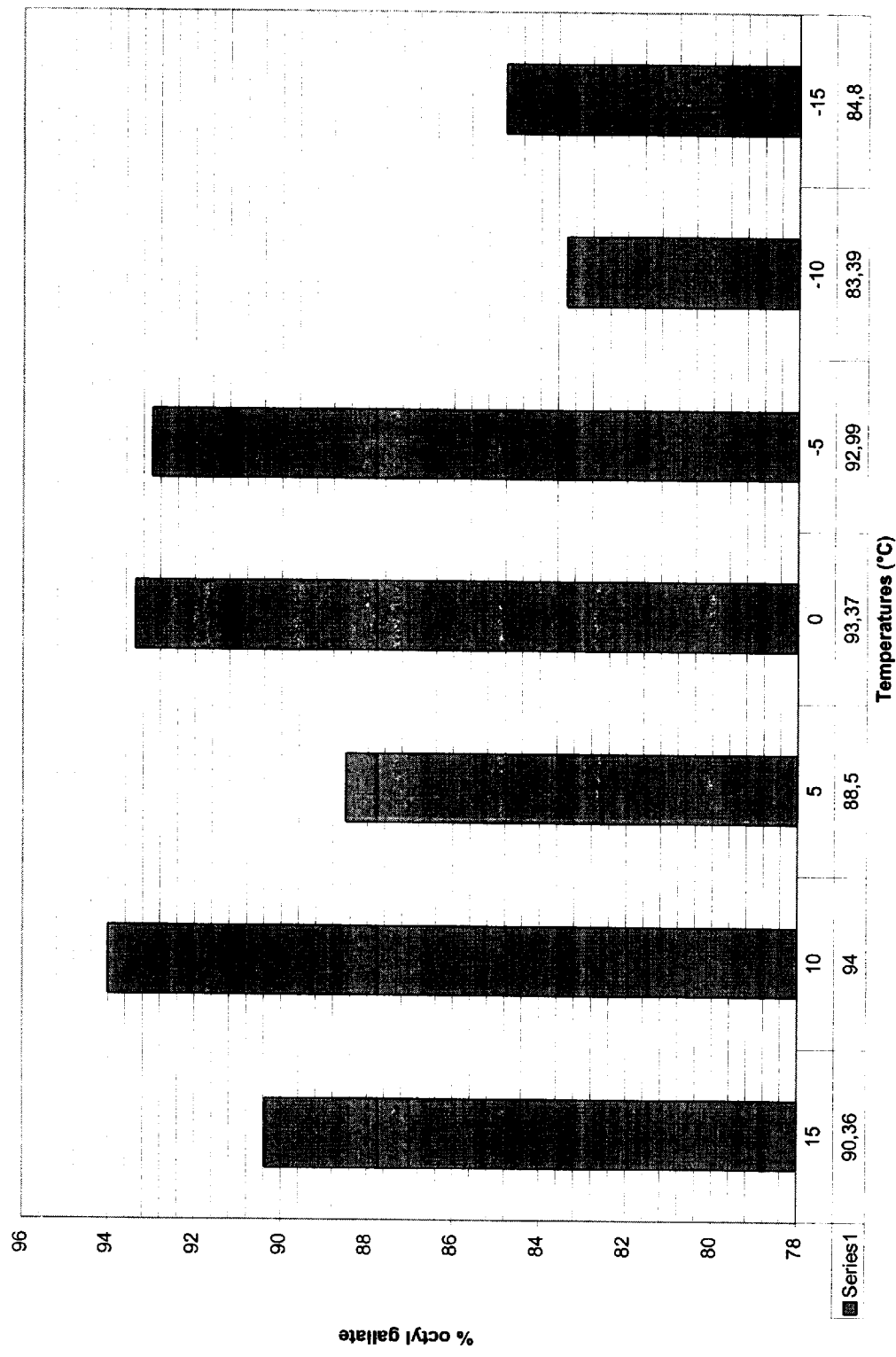
FIG. 7 is a graphical representation of the purity of the reaction product measured at different temperatures used in the crystallization stage.
Figure 8:
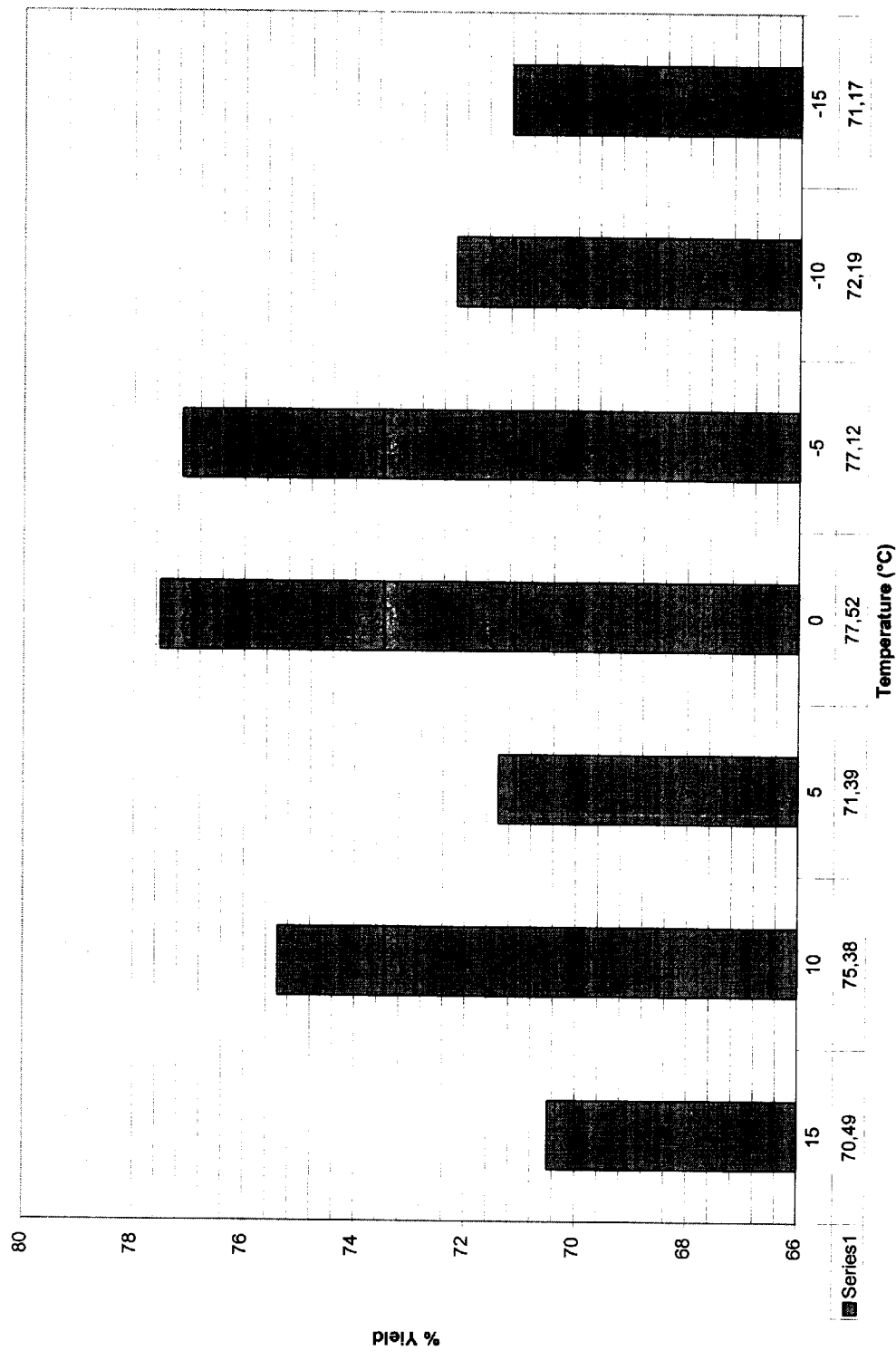
FIG. 8 is a graphical representation of the yield of the reaction product measured at different temperatures used in the crystallization stage.
Figure 9:
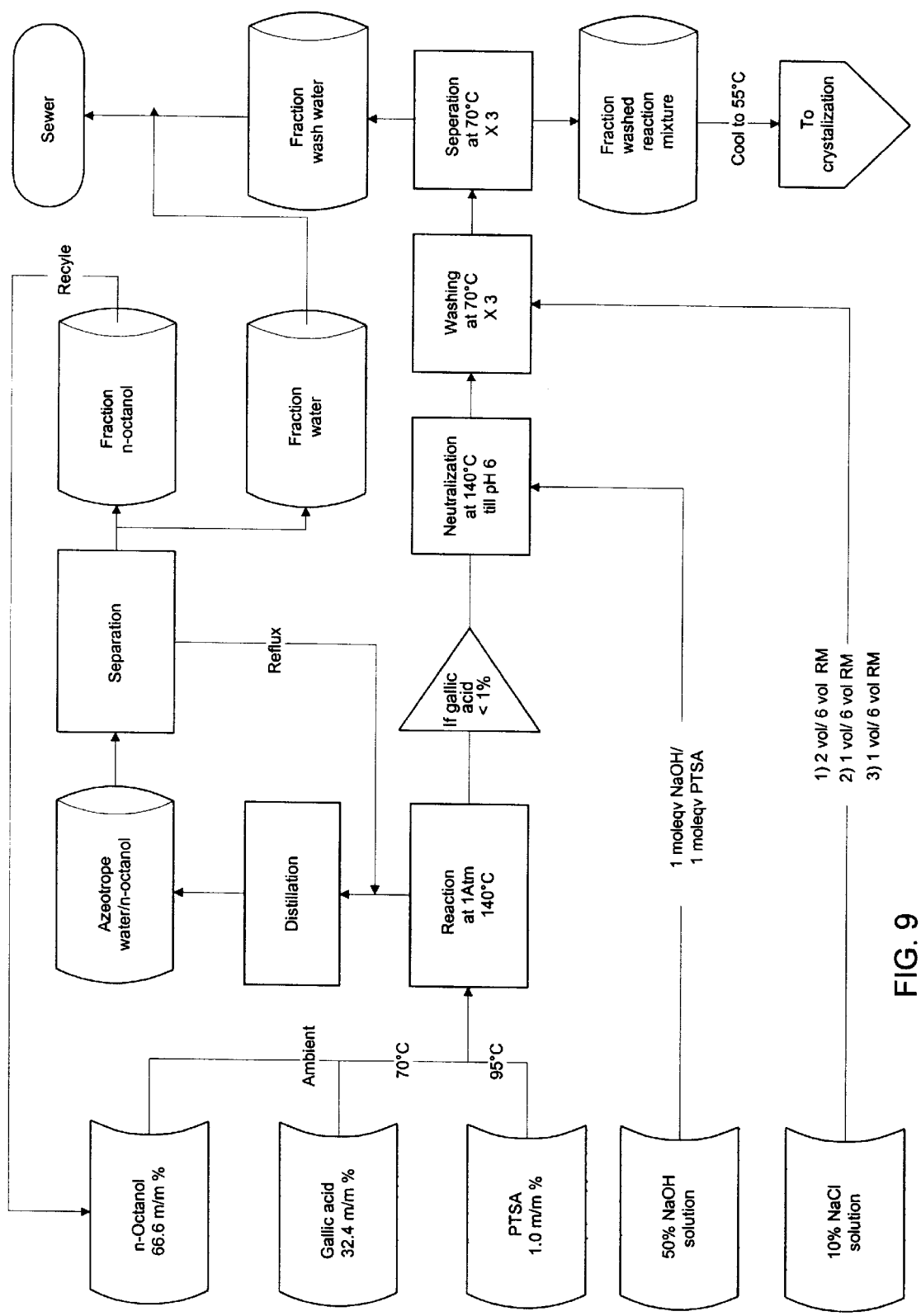
FIG. 9 is a flowchart of the reaction stage of a large-scale process of the present invention.
Figure 10:
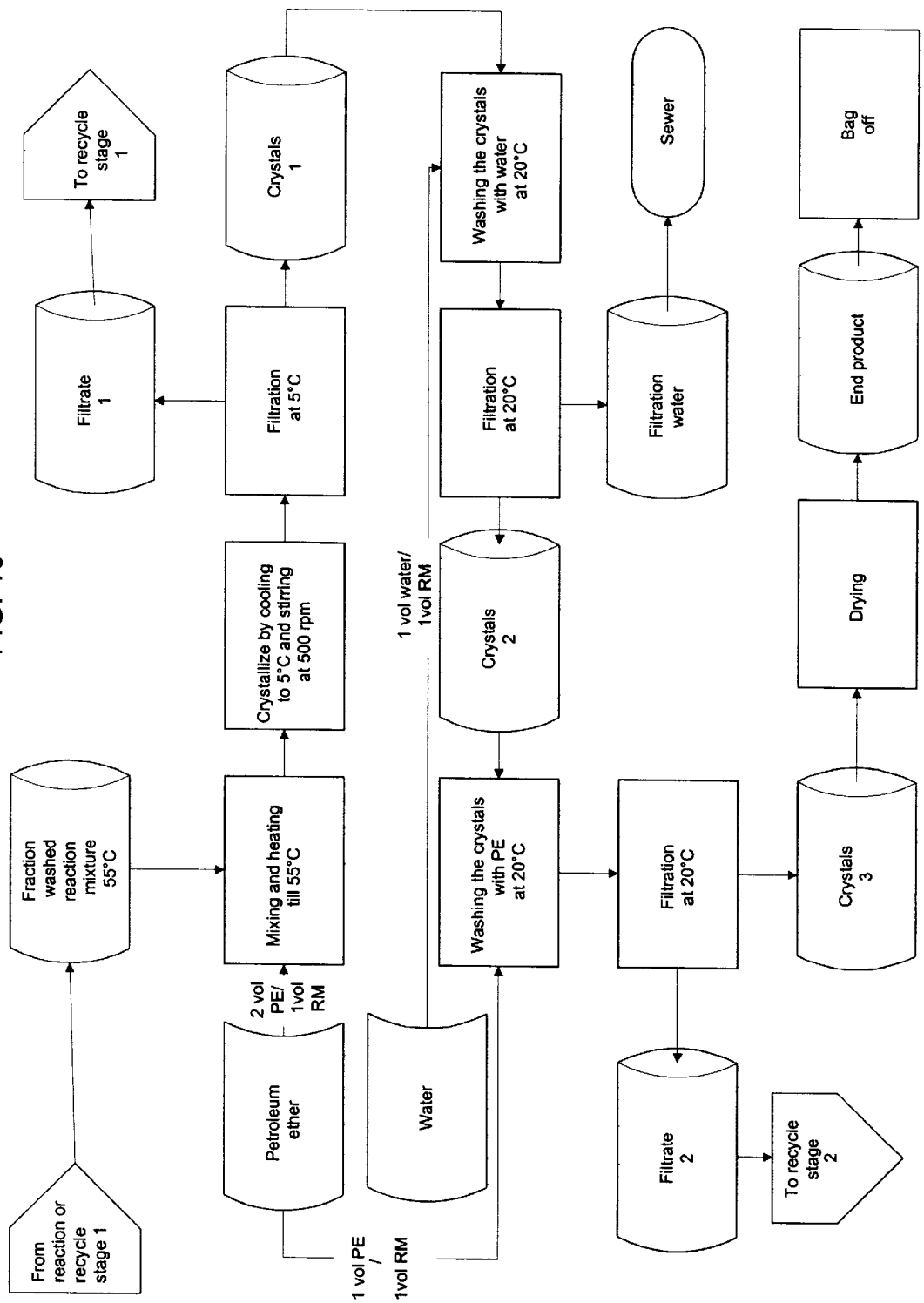
FIG. 10 is a flowchart of the crystallization stage of a large-scale process of the present invention.
Figure 11:
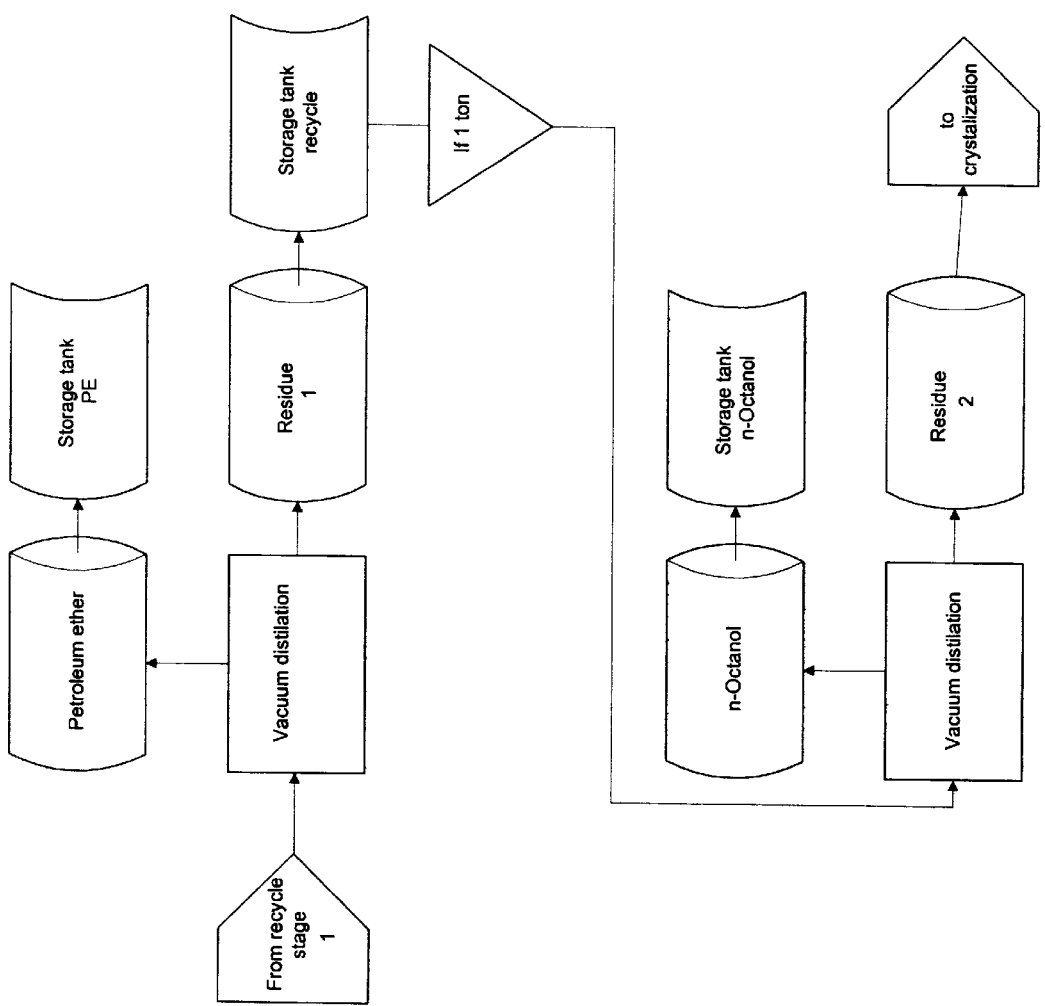
FIG. 11 is a flowchart of a first recycle stage of a large-scale process of the present invention.
Figure 12:
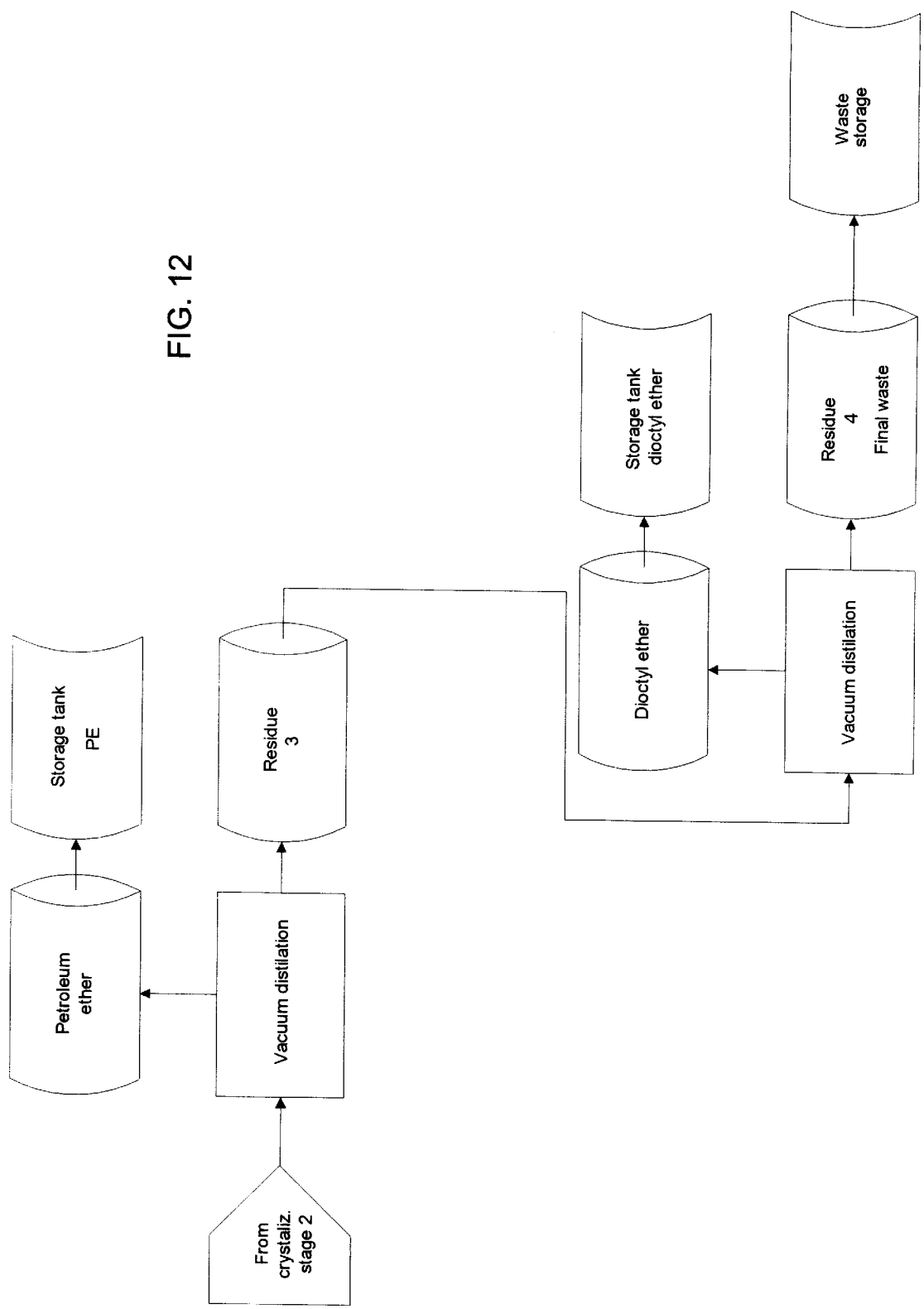
FIG. 12 is a flowchart of a second recycle stage of a large-scale process of the present invention.

The mixture was then cooled while stirring (500 rev/min) from 55° C. to respectively 15° C., 10° C., 5° C., 0° C., −5° C., −10° C. and −15° C. over a period of a minimum of three hours. The octyl gallate slowly crystallized in the petroleum ether. When the mixture reached the selected temperature, that is, 15° C., 10° C., 5° C., 0° C., −5° C., −10° C. and −15° C., respectively, the crystals and mother liquor were separated by means of a Büchner filter (filter: Whatman number 4). The crystals were rinsed with 0.25 volume parts of petroleum ether at 15° C. The crystals were then dried in a vacuum oven at 60° C. and 50 Torr for a period of 12 hours. The purity was checked by measuring the % octyl gallate. The results on purity and yield are presented in FIGS. 7 and 8, respectively.

LARGE-SCALE PROCESS

Utilizing the information generated in the Experiments, a large-scale reaction process was developed and is set out in the flowcharts illustrated in FIGS. 17–20. FIG. 17 is a flowchart of the reaction process. The reaction mixture output from the process of FIG. 17 is input into the crystallization stage, illustrated in FIG. 18. Filtrate 1 is passed from the crystallization stage (FIG. 18) to the first recycle stage process, illustrated in FIG. 19, for the recovery of petroleum ether and octyl alcohol. Residue 2 of the first recycle stage is passed back to the crystallization stage (FIG. 18). Filtrate 2 from the crystallization stage is passed to the second recycle stage, as illustrated in FIG. 20, for the recovery of petroleum ether and dioctyl ether. While some improvement in yield and purity was observed in scaling up of the synthesis, no significant changes in the process described in Experiment 1 were found to be necessary.

EXPERIMENT 6
Large Scale Process

In a reaction vessel, 66.6 kg n-octanol (511.4 mole, 80.5 L) is heated to a temperature of 70° C. Then 33.3 kg (1.77.0 mole) of gallic acid (monohydrate) and 10 kg (5.26 mole) PTSA (monohydrate) are added. This mixture is then submitted to reaction at a temperature of 140° C. and at 1 atm.

pressure. When the reaction is completed, i.e., no more water is being distilled off, the temperature at the top of the distillation column decreases, HPLC analysis of the reaction mixture shows that gallic acid content is less than 1%, the mixture is neutralized to pH=7 by the addition of a 50% NaOH solution. The neutralized reaction mixture is cooled to 70° C., and then washed three times with a 10% NaCl solution at 70° C., once with 66.6 L and twice with 33.3 L. The washed reaction mixture is cooled to 55° C. Two hundred liters of petroleum ether (i.e., approximately twice the volume of the reaction mixture) heated to 55° C. is added to the reaction mixture. The mixture is then cooled to 5° C. while stirring to crystallize the octyl gallate. The mixture is filtered and the crystals are washed at room temperature once with 100 L water and once with 100 L petroleum ether. After filtration, the crystals are dried in vacuo at a temperature that gradually increases from 50° C. to 90° C.

Although the invention has been described with respect to a preferred embodiment thereof, it is to be also understood that it is not to be so limited since changes and modifications can be made therein which are within the full intended scope of this invention as defined by the appended claims.

We claim:

1. A method for crystallizing alkyl gallates from a reaction mixture wherein the alkyl gallate had been formed by esterification of gallic acid, comprising the steps of:
   (a) adding to the reaction mixture a brine solution;
   (b) separating the fraction of the reaction mixture containing the alkyl gallate;
   (c) adding to the separated fraction a solvent;
   (d) cooling said fraction and solvent mixture to produce crystals of the alkyl gallate; and
   (e) filtering said crystals out of said fraction and solvent mixture.

2. A method as defined in claim 1, wherein said solvent is an alkane hydrocarbon.

3. A method as defined in claim 1, wherein said solvent is selected from the group comprising benzene, chloroform, hexane, methylene chloride, petroleum ether, and toluene.

4. A method as defined in claim 1, wherein the order of said alkyl alcohol is greater than 5.

5. A method as defined in claim 1, wherein said brine solution has a concentration of between about 5% and about 20%.

6. A method as defined in claim 1, wherein said brine solution is heated to a temperature of between about 50° C. and about 85° C. before it is added to the reaction mixture.

7. The method of claim 1, wherein said separating and washing steps are repeated.

8. The method of claim 1, wherein said solvent is petroleum ether and the reaction mixture and the petroleum ether are heated to a temperature of between about 40° C. and about 60° C. at the time of adding of the petroleum ether to the reaction mixture.

9. A method as defined in claim 1, wherein said alkyl alcohol comprises octyl alcohol, said catalyst comprises para-toluene sulfonic acid, and said solvent comprises petroleum ether.

10. A method for synthesizing alkyl gallates, comprising the steps of:
    (a) reacting an alkyl alcohol with gallic acid in the presence of an acid catalyst at a temperature of between about 140° C. and about 200° C.;
    (b) removing by distillation water formed in the esterification of the gallic acid;
    (c) heating a solvent to approximately its boiling temperature;
    (d) cooling said reaction mixture to a temperature near the boiling point of said solvent; and
    (e) adding said solvent to form crystals of the alkyl gallate.

11. A method as defined in claim 10, further comprising the steps of filtering and washing said crystals of alkyl gallate.

12. A method as defined in claim 10, further comprising the step of neutralizing the reaction mixture by adding an aqueous alkaline solution prior to the addition of said solvent.

13. A method as defined in claim 12, wherein said neutralization step is carried out when the amount of unreacted gallic acid in the reaction mixture is reduced below about 1%.

* * * * *